(12) United States Patent
Johnston

(10) Patent No.: US 7,312,879 B2
(45) Date of Patent: Dec. 25, 2007

(54) DISTANCE DETERMINATION IN A SCANNED BEAM IMAGE CAPTURE DEVICE

(75) Inventor: Richard S. Johnston, Sammamish, WA (US)

(73) Assignee: University of Washington, Seattle, WA (US)

( * ) Notice: Subject to any disclaimer, the term of this patent is extended or adjusted under 35 U.S.C. 154(b) by 45 days.

(21) Appl. No.: 11/210,465

(22) Filed: Aug. 23, 2005

(65) Prior Publication Data

US 2007/0081168 A1    Apr. 12, 2007

(51) Int. Cl.
*A61B 19/00* (2006.01)
*G01B 11/26* (2006.01)

(52) U.S. Cl. .................. 356/614; 600/476; 600/439; 250/208.1; 250/559.22; 356/621; 356/138; 356/612

(58) Field of Classification Search ............... 356/614, 356/621, 138, 912
See application file for complete search history.

(56) References Cited

U.S. PATENT DOCUMENTS

| 4,527,893 | A |   | 7/1985  | Taylor              |
|-----------|---|---|---------|---------------------|
| 4,677,683 | A |   | 6/1987  | Pferd et al.        |
| 4,767,911 | A |   | 8/1988  | Maram               |
| 4,830,489 | A | * | 5/1989  | Cain et al. ...... 356/73 |
| 4,919,508 | A |   | 4/1990  | Grace et al.        |
| 4,963,018 | A | * | 10/1990 | West ............. 356/3.05 |
| 4,972,344 | A |   | 11/1990 | Stoddard            |
| 4,991,971 | A |   | 2/1991  | Geary et al.        |
| 5,011,259 | A |   | 4/1991  | Lieber et al.       |
| 5,172,685 | A |   | 12/1992 | Nudelman            |
| 5,260,761 | A | * | 11/1993 | Barker .......... 356/4.1 |
| 5,317,148 | A |   | 5/1994  | Gray et al.         |
| 5,400,267 | A |   | 3/1995  | Denen et al.        |
| 5,455,669 | A | * | 10/1995 | Wetteborn ...... 356/5.01 |
| 5,459,570 | A | * | 10/1995 | Swanson et al. ..... 356/479 |
| 5,625,451 | A |   | 4/1997  | Schiff et al.       |

(Continued)

FOREIGN PATENT DOCUMENTS

JP    2004212328 A   *   7/2004

(Continued)

OTHER PUBLICATIONS

Melnyk, Andrew, Photoconductor Detector Technology, Jan. 15, 2002, Encyclopedia of Imaging Science and Technology,John Wiley & Sons, Inc.*

(Continued)

*Primary Examiner*—Layla G. Lauchman
*Assistant Examiner*—Rebecca C. Slomski
(74) *Attorney, Agent, or Firm*—Townsend and Townsend and Crew LLP

(57) ABSTRACT

Methods, systems, and devices can determine spatial relationships between a probe and a target surface. Specular reflections from the target surface vary dramatically with small changes in angle between the scanning beam and the target surface, and as the geometry of the beam scanner and light detector of the probe are often known, and as the angle of the light beam projected from a scanner for accurately generating an image, the pattern of spectral light reflected from the light beam directly back to the detector allows the distance between the probe and the target surface, and/or the angular relationship between the probe and the target surface, to be calculated.

29 Claims, 7 Drawing Sheets

U.S. PATENT DOCUMENTS

| | | | |
|---|---|---|---|
| 5,681,307 | A | 10/1997 | McMahan |
| 5,693,042 | A | 12/1997 | Boiarski et al. |
| 5,727,098 | A | 3/1998 | Jacobson |
| 5,742,718 | A | 4/1998 | Harman et al. |
| 5,764,874 | A | 6/1998 | White |
| 5,768,461 | A | 6/1998 | Svetkoff et al. |
| 5,822,486 | A | 10/1998 | Svetkoff et al. |
| 5,870,511 | A | 2/1999 | Sawatari et al. |
| 5,907,425 | A | 5/1999 | Dickensheets et al. |
| 5,933,240 | A | 8/1999 | Jurca |
| 6,046,720 | A | 4/2000 | Melville et al. |
| 6,069,698 | A * | 5/2000 | Ozawa et al. ............... 356/511 |
| 6,083,166 | A * | 7/2000 | Holdaway et al. .......... 600/439 |
| 6,091,067 | A | 7/2000 | Drobot et al. |
| 6,211,904 | B1 | 4/2001 | Adair et al. |
| 6,222,628 | B1 | 4/2001 | Corallo et al. |
| 6,263,234 | B1 * | 7/2001 | Engelhardt et al. ......... 600/476 |
| 6,294,775 | B1 * | 9/2001 | Seibel et al. ............. 250/208.1 |
| 6,327,493 | B1 | 12/2001 | Ozawa et al. |
| 6,329,778 | B1 | 12/2001 | Culp et al. |
| 6,388,641 | B2 | 5/2002 | Tidwell et al. |
| 6,402,743 | B1 | 6/2002 | Orszulak et al. |
| 6,411,838 | B1 | 6/2002 | Nordstrom et al. |
| 6,492,962 | B2 | 12/2002 | Melville et al. |
| 6,498,948 | B1 | 12/2002 | Ozawa et al. |
| 6,563,105 | B2 | 5/2003 | Seibel et al. |
| 6,564,087 | B1 | 5/2003 | Pitris et al. |
| 6,626,834 | B2 | 9/2003 | Dunne |
| 6,627,903 | B1 | 9/2003 | Hirayanagi |
| 6,666,860 | B1 | 12/2003 | Takahashi |
| 6,845,190 | B1 | 1/2005 | Smithwick et al. |
| 7,184,150 | B2 * | 2/2007 | Quadling et al. ........... 356/602 |
| 2001/0030744 | A1 | 10/2001 | Chang |
| 2001/0055462 | A1 | 12/2001 | Seibel |
| 2002/0064341 | A1 | 5/2002 | Fauver et al. |
| 2002/0131052 | A1 | 9/2002 | Emery |
| 2003/0010826 | A1 | 1/2003 | Dvorkis et al. |
| 2003/0086161 | A1 | 5/2003 | Harris |
| 2003/0103199 | A1 * | 6/2003 | Jung et al. .................... 356/73 |
| 2003/0179428 | A1 | 9/2003 | Suzuki et al. |
| 2004/0076319 | A1 | 4/2004 | Fauver et al. |
| 2004/0113059 | A1 | 6/2004 | Kawano et al. |
| 2004/0254474 | A1 | 12/2004 | Seibel et al. |
| 2006/0072843 | A1 | 4/2006 | Johnston et al. |
| 2006/0072874 | A1 | 4/2006 | Johnston et al. |
| 2006/0138238 | A1 | 6/2006 | Johnston et al. |
| 2006/0186325 | A1 | 8/2006 | Johnston et al. |

FOREIGN PATENT DOCUMENTS

| | | |
|---|---|---|
| WO | WO 00/75712 | 12/2000 |

OTHER PUBLICATIONS

"Engineering Study of an Endoscope Design," *Human Interface Technology*, <www.hitl.washington.edu/research/endoscope/> (Sep. 30, 2004).

"Micro-Optical Fabrication of a Fiber Scanning System," *Human Interface Technology*, <www.hitl.washington.edu/projects/mfabfiber/> (Sep. 29, 2004).

"Q factor" from *Wikipedia, The Free Encyclopedia*, May 20, 2004, <www.en.wikipedia.org/wiki/Q_factor> (Jun. 22, 2004).

Andersen, J. and Seibel, E., "Real-Time Hazard Detection Via Machine Vision for Wearable Low Vision Aids," *5th Intl. Symposium on Wearable Computers, Proceedings of IEEE ISWC* 2001, pp. 182-183.

Brown, C. et al., "A Novel Design for a Scanning Fiberoptic Endoscope," *Human Interface Technology Laboratory, University of Washington*, Seattle, WA 98195-2142 and *Mechanical Engineering Department, University of Washington*, Seattle, WA 98195, no date.

Brown, C. et al., "Mechanical Design and Analysis for a Scanning Fiber Endoscope," *ASME International Mechanical Engineering Congress and Exposition*, New York, NY, Nov. 11-16, 2001, BED-vol. 50:165-166.

Fauver, M. et al., "Microfabrication of Fiber Optic Scanners," in Proceedings of Optical Scanning II, *SPIE*, 4773:102-110 (2002).

Johnson, B., "Grating Shrinks Endoscope," *Photonics Spectra*, (Oct. 2003), <www.photonics.com/spectra/applications/QX/ASP/aoaid.335/QX/read.htm> (Sep. 30, 2004).

Johnston, R. et al., U.S. Appl. No. 11/094,017, filed, Mar. 29, 2005.

Melville, C., U.S. Appl. No. 11/187,744, filed Jul. 21, 2005.

Piyawattanametha, W. et al., "A MEMS Non-Interferometric Differential Confocal Scanning Optical Microscope," *Transducers 2001 & Eurosensors XV*, Munich, Germany, Jun. 10-14, 2001, 4 pages.

Seibel, E. and Smithwick, Q., "Single Fiber Flexible Endoscope: General Design for Small Size, High Resolution, and Wide Field of View," *Proceedings of the SPIE, Biomonitoring and Endoscopy Technologies*, 4158:29-39 (2001).

Seibel, E. and Smithwick, Q., "Unique Features of Scanning Fiber Optical Endoscopy," presented at the 2000 Annual Fall Meeting of the Biomedical Engineering Society, BMES, Seattle, WA, Oct. 12-14, 2000, *Annals of Biomedical Engineering*, vol. 28, Suppl. 1, S-40.

Seibel, E. et al., "Prototype Scanning Fiber Endoscope," presented at *SPIE BiOS*, San Jose, CA (Jan. 2002).

Seven, R., "At the UW Hit Lab, There's Virtue in Virtual Reality," Seattletimes.com, Apr. 11, 2004, <www.seattletimes.nwsource.com/pacificnw/2004/0411/cover/html> (Jun. 9, 2004).

Smithwick, et al., "Modeling and Control of a Resonant Fiber Scanner for Laser Scanning Display or Acquisition," *Department of Aeronautics and Astronautics and Human Interface Technology Laboratory, University of Washington*, PowerPoint presentation (33 pages), May 22, 2003.

Smithwick, et al., "Modeling and Control of the Resonant Fiber Scanner for Laser Scanning Display or Acquisition," *SID 03 Digest*, 34:1455-1457 (2003).

Smithwick, Q. et al., "Control Aspects of the Single Fiber Scanning Endoscope," Proceedings of SPIE vol. 4253 International Symposium on BiOS 2001, *Optical Fibers and Sensors for Medical Applications*, 4253:176-188.

Smithwick, Q. et al., "Depth Enhancement Using a Scanning Fiber Optical Endoscope," Optical Biopsy IV, Ed. Robert R. Alfano, *Proc. of SPIE*, vol. 4613:222-233 (2002).

Tearney, G. et al., "Scanning Single-Mode Fiber Optic Catheter-Endoscope for Optical Coherence Tomography," *Optics Letters*, 21(7):543-545 (Apr. 1, 1996).

Wang, W. et al., "Development of an Optical Waveguide Cantilever Scanner," Opto-Ireland 2002: Optics and Photonics Technologies and Applications, *Proc. SPIE*, 4876:72-83 (2003).

Wang, W. et al., "Micromachined Optical Waveguide Cantilever as a Resonant Optical Scanner," *Sensors and Actuators A*, 102:165-175 (2002).

* cited by examiner

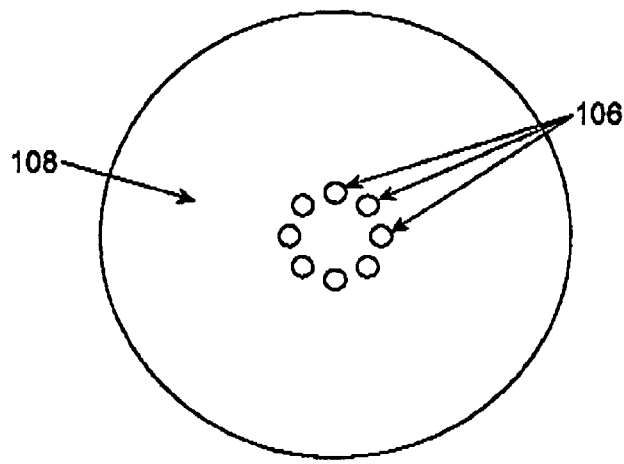
FIG. 7
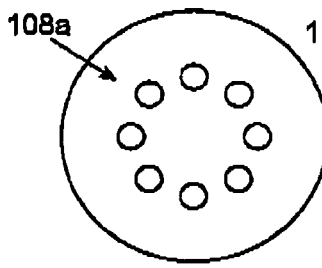 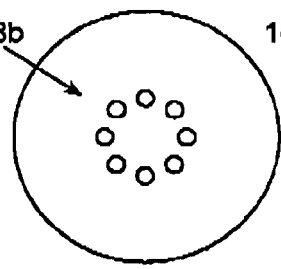 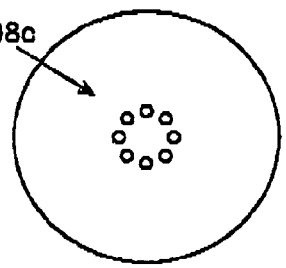
FIG. 8A  FIG. 8B  FIG. 8C
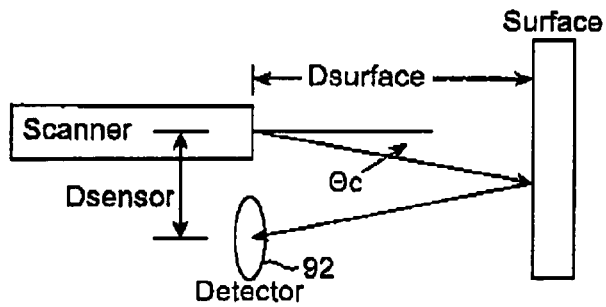
FIG. 9

DISTANCE DETERMINATION IN A SCANNED BEAM IMAGE CAPTURE DEVICE

BACKGROUND OF THE INVENTION

The present invention is generally related to scanning beam devices, systems, and methods. More specifically, the present invention can provide distance measurements, angle measurements, and/or other geometrical relationships between a scanned beam device and a surface, such as between a scanning fiber endoscope and an internal tissue, typically by identifying specular reflection signals from the surface.

There is a growing market for micro-optical devices, and particularly for small image acquisition systems (e.g., cameras). Micro-optical systems having appropriate optical characteristics and size may find use in a variety of applications including minimally invasive medical imaging (and particularly in flexible endoscopes), in surveillance, in industrial inspection and repair, in machine and robotic vision systems, in micro-barcode scanners, and the like. Scanning beam systems may fill the needs in some or all of these applications, although challenges remain in providing the desired optical characteristics at a reasonable cost.

An improved scanning beam system has been under development at the University of Washington to more fully meet the needs for micro-optical image acquisition systems. This improved scanning beam system makes use of a cantilevered optical fiber that can be scanned in one or two dimensions. Light is projected out of the end of the optical fiber, through a lens system, and onto a target area of a surface. To acquire an image, a time series of backscattered reflected light is captured with one or more light detector(s) of the system. More specifically, signals from one or more photodetector(s) correspond to the brightness of the small portion of the image illuminated by the fiber at that point in time. As the motion of the optical fiber is predictable and repeatable, the reflected backscattered light intensity measured at the detector(s) can be sequentially correlated with known positions of the optical fiber. This allows a two-dimensional image to be generated one pixel at a time. Some exemplary scanning fiber devices are described in U.S. Pat. No. 6,294,775B1 (Seibel) and U.S. Pat. No. 6,563,105B2 (Seibel), and in U.S. Patent Application Publication Nos. 2001/0055462A1 (Seibel) and 2002/0064341A1 (Seibel), the complete disclosures of which are incorporated herein by reference.

The images obtained by a scanning fiber endoscope or other scanning fiber device are two-dimensional. In other words, these images appear similar to an image taken with a traditional camera. Hence, these images may contain somewhat limited depth information. Nonetheless, in comparison to traditional image capture devices, the new scanning fiber technology offers many advantages. The small mass of the optical fiber allows high scan angles at video rates. Optical fiber scanners also have a small volume, optionally being packaged into a cylinder having a diameter of less than 1 mm. The optical capabilities and small package size make these new scanning beam devices particularly beneficial for use in endoscopes.

While scanning fiber systems appear to be very promising for use in a number of different applications, additional improvements would still be desirable. For example, distance and other geometrical information can be very useful when working with an endoscope. It would be particularly valuable for an operator to know a distance between, for example, the tip of an endoscope and a tissue surface or tissue structure being viewed. Additional geometrical information regarding the tissue surface or structure may also be of use.

In light of the above, it would generally be desirable to provide improved scanned beam devices, systems, and methods. It would be particularly desirable if these improved devices could provide distance measurement and/or other geometric information, preferably in combination with the imaging capabilities of the recently developed scanning fiber devices. Ideally, this additional geometrical information might be provided without significantly increasing the size, complexity, or cost of these advantageous new image capturing devices.

BRIEF SUMMARY OF THE INVENTION

The present invention provides methods, systems, and devices for determining spatial relationships between a probe and a target surface. Embodiments of the invention will take advantage of specular reflections from the target surface. Unlike the diffuse backscatter reflections upon which much of the image in a scanned beam device is typically based, these specular reflections typically vary dramatically with small changes in angle between the scanning beam and the target surface. As the geometry of the beam scanner and light detector of the probe are known, and as the angle of the light beam projected from the scanner is often used for accurately generating an image, the pattern of spectral light reflected from the target surface back to the detector(s) may allow the distance between the probe and the target surface, and/or the angular relationship between the probe and the target surface, to be calculated. Conveniently, the specular reflections are typically readily identified and separated from the diffuse reflected light from which an image is primarily formed, as the specular reflections will often be significantly brighter than the diffuse reflected light. Hence, the spatial relationships can be determined without adding significant mechanical complexity or bulk to scanning beam imaging devices such as the new scanning fiber endoscopes.

In a first aspect, the invention provides a method for determining a spatial relationship between a probe and a target surface. The method comprises oscillating a beam of light from the probe spatially across the surface. A specular reflection of the light from the surface is sensed with a light detector of the probe. A distance between the surface and the probe, and/or an angle between the surface and the probe is determined using the sensed specular reflection.

The probe will often comprise an endoscope, the surface often comprising a tissue surface within a patient body. The beam may be oscillated by vibrating an optical fiber with a two-dimensional scan (such as a spiral or the like), and the probe will often transmit image signals for imaging of the tissue surface in response to diffuse reflection of the light beam from the tissue surface. Both the diffuse light and specular light may be detected by the detector of the probe. Specular image signals may be separated from display image signals using a difference in brightness between these two different forms of reflected light. The spatial relationship may be determined using these separated specular image signals, such as by analyzing a centroid of a specular reflection, a pattern of specular reflections received by a plurality of detectors, a shape of a specular reflection, or the like. As the specular reflection may be located in a relatively small portion of the overall imaging field of view, an angular scan magnitude may be reduced when measuring the specular reflection so as to enhance measurement resolution.

Typically, the distance or angle will be determined at least in part from an angle of the oscillating beam when the specular reflection is sensed. The beam will be oscillated with a scanner, and the distance between the probe and the surface may be determined, for example, using a scanner/detector distance between, for example, a center of the scanner and the detector. In some embodiments, the specular reflection may be sensed with a plurality of light detectors of the probe, so that a pattern of spectral reflections from the surface are determined. The distance may be determined in response to a spectral reflection pattern size, and/or in response to a single spectral reflection from an associated single detector, so that a plurality of distances may optionally be measured when using multiple detectors. Where the detectors are at different distances from the center of the scan, additional information regarding the angle and/or geometry of the target surface can be identified. Similarly, when the angle of the surface is determined relative to the probe, the angle may be determined at least in part from a shape of an individual specular reflection received at a single detector, a shape of a pattern of spectral reflections received by a plurality of detectors, a size of an individual spectral reflection or pattern of spectral reflections, or the like. By measuring the angle of the surface relative to the probe at a plurality of locations within a field of view of the probe (for example, by using a probe having a plurality of detectors, or by moving at least a portion of the probe between two different measurements), a map of the target surface geometry may be generated. In some embodiments, the entire probe may move, with the system identifying one or more datum locations in the images before and after the movement so as to accurately combine the two separate measurements.

While generally described as being based on an image, it should be understood that a plurality of spectral reflection images may be combined (such as by averaging the images) so as to enhance image accuracy. Individual diffuse and/or spectral images may be generated at a rate of at least 1 frame per second, often being 15-30 frames per second.

In another aspect, the invention provides a surface measurement system. The system comprises a light source transmitting a beam of light. A scanner is coupled to the light source, and spatially oscillates the beam of light over a surface. A light detector detects a specular reflected portion of the light from the surface. A processor is coupled to the detector, and determines a distance between the surface measurement system and the surface, or an angle of the surface relative to the surface measurement system. In many cases, both the distance and angle will be determined. Regardless, the processor will make use of the specular reflected light to determine this spatial information.

The system may be configured to employ one or more of the method steps described herein, with at least a portion of the processor typically comprising a machine-readable code embodying instructions for performing at least a portion of these methods. The scanner, light detector, and/or the like of the surface measurement system may be included within an endoscopic probe body. The scanner may comprise an assembly including a fiber and an actuating system for oscillating the fiber in first and second dimensions. Hence, the assembly may be suitable for use in a scanning fiber endoscope system.

The processor may comprise a light separator module configured to separate the specular reflected light from the dispersed reflected light. A display may be coupled to the processor, the display showing an image of the surface generating using the dispersed reflected light. The display (or some other output) may indicate the spatial measurements obtained using the surface measurement system.

In another aspect, the invention provides software for use in a scanned beam imaging system. The system includes a scanner for spatially oscillating a beam of light over a target surface, and a detector for detecting reflected light from the surface. The system also includes a processor coupled to the detector. The software comprises machine-readable code embodying instructions for determining a distance between the system and the surface, or an angle of the surface relative to the system. In either case, the code will provide instructions for making the determination from a specular portion of the reflected light, with the code preferably indicating both the distance and angle.

BRIEF DESCRIPTION OF THE DRAWINGS

FIG. 7 illustrates a spectral reflection pattern obtained using the probe of FIGS. 6A and 6B.

FIGS. 8A-8C schematically illustrate alternative spectral reflection patterns at differing separation distances between the probe and target surface.

FIG. 9 illustrates calculation of a distance between the probe and target surface.

DETAILED DESCRIPTION OF THE INVENTION

The present invention generally provides improved scanned beam devices, systems, and methods. The improved scanned beam techniques will often provide spatial information (such as separation distance, an angle, or even a contour map) of a target surface, typically using spectral reflections from the target surface.

The scanning beam systems of the present invention will often include a scanning beam device or probe and a base station for controlling the scanning beam device. The scanning beam devices may take on a variety of forms, but will typically comprise a flexible or rigid endoscope, catheter, fiberscope, microscope, boroscope, or the like. The scanning beam devices may have a limited life (e.g., being disposable) or may be multiple-use devices. If the device is for medical use, the scanning beam devices will generally be sterile, either being sterilizable or being provided in hermetically sealed packages for use.

The scanning beam devices or probes will often include a scanner for spatially scanning a beam of light over a target area of a target surface. The scanner preferably comprises a single, cantilevered optical fiber. While these scanning beam systems and scanning fiber systems generally encompass systems used for image acquisition, alternative embodiments may be used at least in part (or even primarily) for image display. Scanning beam and scanning fiber display systems may, for example, selectively project illuminating light from the end of the scanning fiber so as to generate an image on the target surface. While the exemplary embodiments of the distance and/or angle measurement systems will often be described with reference to a scanning fiber device, alternative beam scanning mechanisms may also be employed. For example, mirror beam scanning systems and/or micro electromechanical systems (MEMS) beam scanning mechanisms may be suitable for effecting the scanning of the beam in some embodiments.

Figure 1:
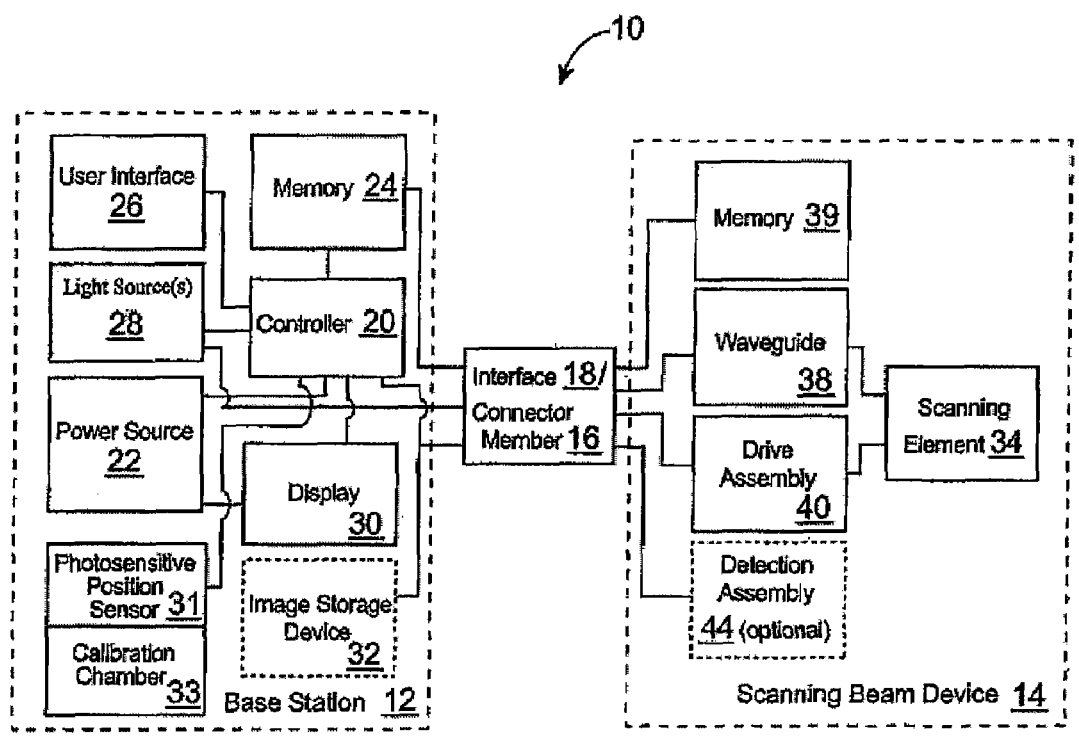
FIG. 1 schematically illustrates a simplified scanning beam system that may comprise an embodiment of the present invention.

FIG. 1 is a block diagram of a scanning beam system 10 that may embody the present invention. Scanning beam system 10 includes a base station 12 and a scanning beam device 14. The scanning beam device 14 includes a connector member 16 that is configured to mate with an input interface 18 on the base station. Coupling with the connector member 16 to the input interface 18 may create a power path, drive signal path, detector path, illumination path, and/or data communication path between elements of the base station 12 and the related elements of the scanning beam device 14.

As shown in FIG. 1, base station 12 typically includes a controller 20 that has one or more microprocessors and/or one or more dedicated electronic circuits which may include a gate array (not shown) to control the actuation of the scanning beam device 14 and generation of the images. Controller 20 may also include scanner drive electronics, detector amplifiers, digital/analog (D/A) converters, and A/D converters (not shown). The drive electronics in controller 20 and the software modules stored in memory may be used to provide a customized control routine for the scanning beam device 14. As will be appreciated by those with skill in the art, the structure of controller 20 may include (and the methods of the present invention may be carried out by) a wide variety of combinations of hardware and/or software. In many embodiments, a combination of electronic hardware will be used in combination with one or more software programs, with the software typically being embodied in a tangible media (such as a random access memory, a read-only memory, a floppy disk, an optical disk, a hard disk, and/or the like) embodying machine-readable code with programming instructions for carrying out one, some, or all of the method steps for one or more of the methods described herein.

Controller 20 is in communication with a plurality of components within the base station 12 via a communication bus (not shown). The communication bus typically allows for electrical communication between controller 20, a power source 22, a memory 24, a user interface 26, one or more light sources 28, one or more output displays 30, and a photosensitive position sensor 31 that is coupled to a calibration chamber 33. Optionally, if the scanning beam device 14 includes a detector assembly, the base station 12 may include a separate image storage device 32 in communication with controller 20. In alternative embodiments, the image storage device 32 may simply be a module within memory 24, which may also be integrated into controller 20. As can be appreciated, the specific configuration of base station 12 may vary depending on its intended use and the like, so that the base station may include fewer or more modules or elements than illustrated in FIG. 1. The various hardware and/or software modules illustrated in FIG. 1 may generally be separated in a variety of alternative configurations, combined into fewer modules, and the like.

Depending on the particular configuration of scanning beam device 14, light source 28 may emit a continuous stream of light, modulated light, or a stream of light pulses. Base station 12 may comprise a plurality of different light sources 28, so as to be able to operate different scanning beam devices that have different illumination capabilities. The light sources 28 may include one or more of a red light source, a blue light source, a green light source (collectively referred to herein as a "RGB light source"), an IR light source, UV light source, and/or high intensity laser source (typically for a therapeutic scanning beam device). The light source(s) 28 may be configured to be switchable from a first mode (e.g., continuous stream) and a second mode (e.g., a stream of light pulses). For ease of reference, other conventional elements in the light source need not be shown. For example, if a RGB light source is used, the light source may include a combiner to combine the different light before it enters the scanning element of the scanning beam device 14.

Memory 24 may be used for storing the software elements of the functional modules, lookup tables, counterbalancing control algorithms, and other algorithms that control the operation of and/or calibration of the scanning beam device 14. The control routine used by the controller 20 for controlling and counterbalancing the scanning beam device 14 will typically be configurable so as to match the operating parameters of the attached device (e.g., resonant frequency, voltage limits, zoom capability, color capability, etc.). As noted below, memory 24 may also be used for storing the image data received from the detector assembly 44 of the scanning beam device, remapping lookup tables and algorithms, remapping drive signals, parameters of the scanning beam device, etc. The detector assembly 44 will typically include one or more photodetectors to generate electrical signals in response to light signals impinging on a detector surface. The photodetectors may be coupled to the detector surface by an optical waveguide such as an optical fiber, so that the photodetectors may be mounted in device 14, in base station 12, in input interface 18, or the like. The detectors and their locations described herein will encompass the detector surfaces and their locations.

Conventional elements of base station 12 may also be included, and need not be shown in FIG. 1. For example, embodiments of base station 12 may include amplifiers, clocks, waveform generators, and the like. A more complete description of a suitable base station and its interaction with the scanning beam device may be found in the following commonly owned U.S. patents and patent applications: U.S. patent application Ser. No. 10/956,241, entitled "Remapping Methods to Reduce Distortions in Images," filed Oct. 1, 2004, U.S. patent application Ser. No. 10/956,473, entitled "Configuration Memory for a Scanning Beam Device," filed Oct. 1, 2004, U.S. patent application Ser. No. 11/021,981, entitled "Methods of Driving a Scanning Beam Device to Achieve High Frame Rates," filed on Dec. 23, 2004, U.S. patent application Ser. No. 11/021,981, entitled "Methods of Driving a Scanning Beam Device to Achieve High Frame Rates," filed on Dec. 23, 2004, and U.S. patent application Ser. No. 11/065,224, entitled "Scanning Beam Device with Detector Assembly," filed on Feb. 23, 2005, the complete disclosures of which are incorporated herein by reference.

Scanning beam device 14 includes a scanning element 34 for delivering and scanning a beam of light onto the target area. A wave guide 38, typically in the form of an optical fiber (which may be a continuation of scanning element 34), is optically coupled to the light source 28, so as to deliver illumination from the light source to the scanning element. An actuator or drive assembly 40 is coupled to the scanning element 34 and is adapted to actuate the scanning element 34 according to a drive signal received from controller 20. Optionally, the scanning beam device 14 may include a non-volatile memory 39 for storing identification data or parametric data of the scanning beam device. While not shown in FIG. 1, the scanning beam device 14 will typically include an optical assembly that directs an focuses the light from a distal tip of the scanning element 34.

Figure 2:
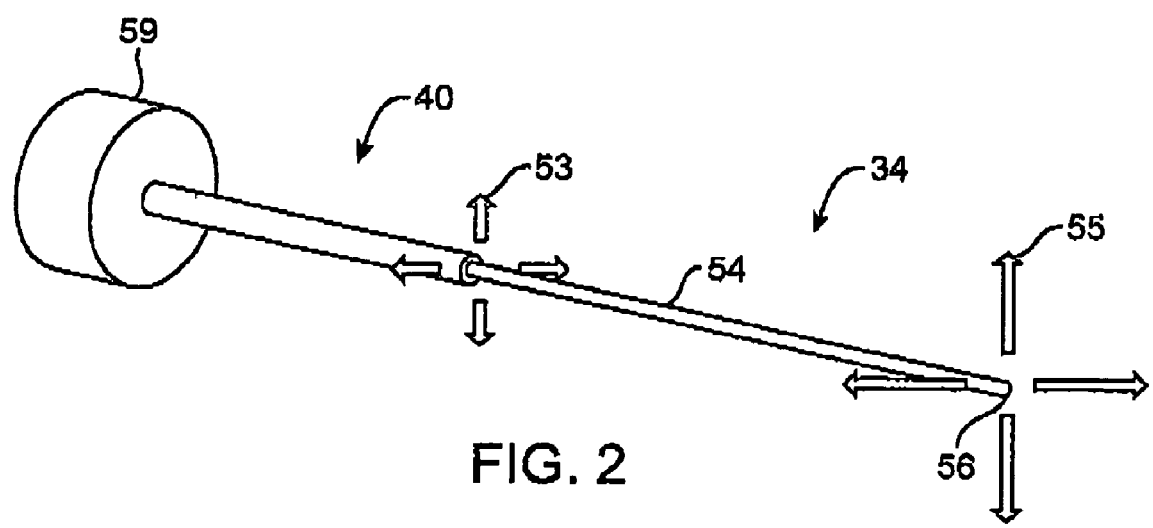
FIG. 2 is a close-up of distal end of a scanner, showing a drive assembly and a scanning element in the form of an optical fiber for use in the system of FIG. 1.

In an exemplary embodiment illustrated in FIG. 2, the scanning element 34 comprises a cantilevered optical fiber, with drive assembly 40 comprising a piezoelectric tube bender. The optical fiber 34 may include a proximal portion extending proximally of drive assembly 40 and a distal portion 54 including a distal tip 56. Optical fiber 34 is typically affixed along at least one point of the optical fiber so as to be cantilevered such that the distal portion 54 is free to be deflected in a desired scan pattern. The proximal portion of the optical fiber can function as a wave guide so as to transmit light from light source 28 (see FIG. 1). In other embodiments, a separate wave guide may be optically coupled to the proximal portion of the optical fiber 34 so that illumination from light source 28 will be directed into the core of optical fiber 34 and out of distal tip 56.

Optical fiber 34 may have a variety of alternative dimensions and cross-sectional profiles. Depending on the desired characteristics of the device, optical fiber 34 may have a symmetrical cross-sectional profile or an asymmetrical cross-sectional profile. Optical fiber 34 may have a round cross-sectional fiber with substantially the same resonance characteristics about any two orthogonal axes. Asymmetric cross-sectional optical fiber profiles (e.g., an ellipse) may have different resonant frequencies about their major and minor axes. If desired, the optical fiber 34 may be linearly or non-linearly tapered along at least a portion of its longitudinal length.

To achieve the deflection of the distal portion 54 of optical fiber 34, the cantilevered distal portion of the optical fiber may be coupled to the drive assembly 40, which is shown in FIG. 2 as a cylindrical, piezoelectric tube bender. Drive assembly 40 will typically move in one or two dimensions (as indicated by arrows 53) at a frequency that is within a Q-factor of the resonant frequency of the distal portion of the optical fiber, and preferably at its mechanical or vibratory resonant frequency (or at one or more harmonics of the resonant frequency). Scanning element 34 need not be driven at substantially the resonant frequency, although if scanning element 34 is not scanned at its resonant frequency, a larger amount of energy may be needed to provide a desired radial displacement for the scan pattern.

The exemplary piezoelectric drive assembly 40 receives a drive signal from controller 20, the drive signal causing the piezoelectric drive assembly to deflect the distal tip 56 of the optical fiber 34 so that an illumination spot is scanned in a desired scan pattern over the target surface. Alternative drive assemblies may comprise one or more permanent magnets, electromagnets, an electrostatic drive, a sonic drive, an electromechanical drive, or the like. Drive assembly 40 and/or scanning element 34 will often scan the light spot from tip 56 with a scan that substantially originates at a point space along the optical path distal of a drive assembly support or mass 59, the scan often having a scan center along a centerline of a lens system distal of the optical fiber (see FIGS. 6A and 9), with the scan center optionally being within a lens or lens system. In other words, the scanning of the light beam from the scanning beam device may at least roughly be modeled as being deflected from a point in space distal of scanning element 34.

Figure 3:
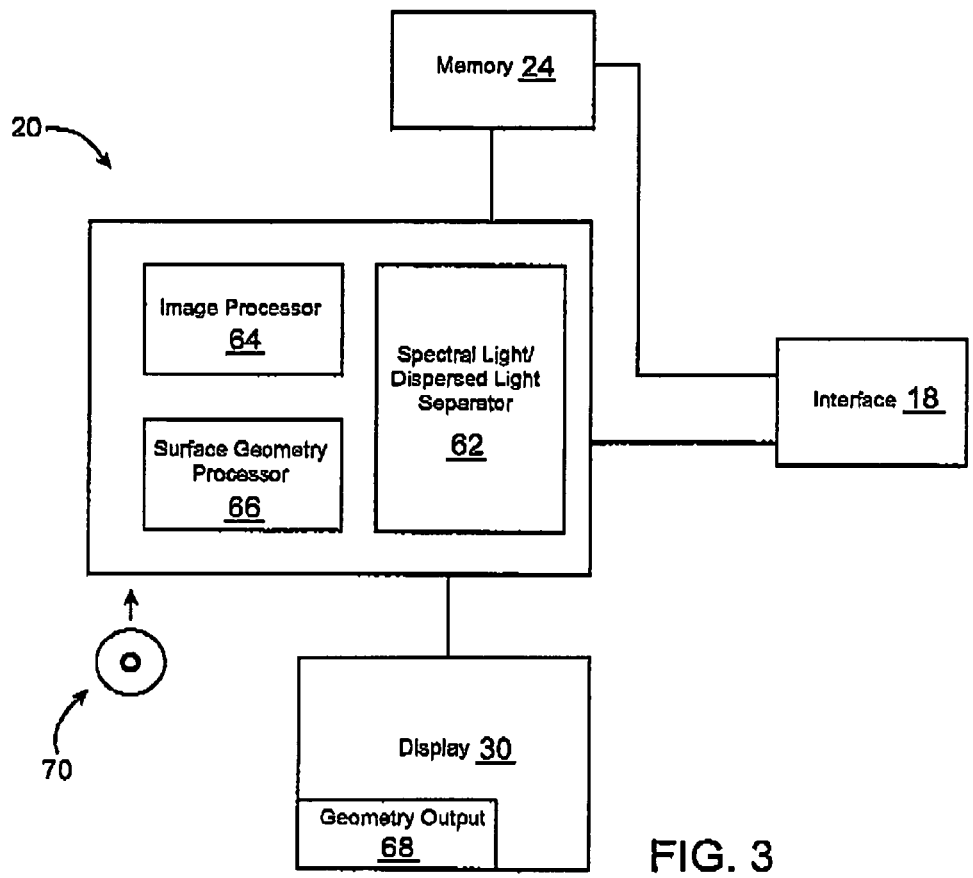
FIG. 3 schematically illustrates additional details of the controller of the system of FIG. 1, along with associated components.

Referring now to FIG. 3, additional aspects of the controller 20 are shown schematically. So as to facilitate both imaging and distance measurement using system 10 (see FIG. 1), controller 20 includes a separator 62 for separating a spectral portion of the light received by a detector of scanning beam device 14 from a diffuse portion of the reflected light. Signals generated by the diffuse light portion are transmitted to an image processor 64, while the spectral light portion is transmitted to a surface geometry processor 66. Image data from the image processor will generally be output by display 30. Geometry processor 66 may also transmit data to display 30, optionally with a portion of the display being dedicated to a geometrical data output 68. Geometry information can alternatively be superimposed on the image information in the display, or may be separated to be shown on a different display or at a different time than the image data.

While image processor 64 may primarily make use of the dispersed light portion, the image processor may also make use of spectral light. Similarly, the surface geometry processor 66 may make some use of the dispersed light signals from separator 62. The separator 62, image processor 64, and surface geometry processor 66 may again comprise modules including hardware and/or software. Conveniently, programming so as to take advantage of the measurement systems and methods described herein with existing scanned beam imaging systems may be input into controller 20 of an existing base station 12 (see FIG. 1) using a tangible media 70 such as an optical disk (including a CD or DVD), a magnetic recording media (such as a floppy disk or removable hard disk), an internet, an Ethernet, a wireless network connection, or the like. While existing scanning beam devices 14 may be employed, alternative scanning beam devices with structures configured for the measurements described herein may be provided for use with such existing imaging base systems modified with this new programming code so as to provide distance and/or angle measurement capabilities.

Figure 4:
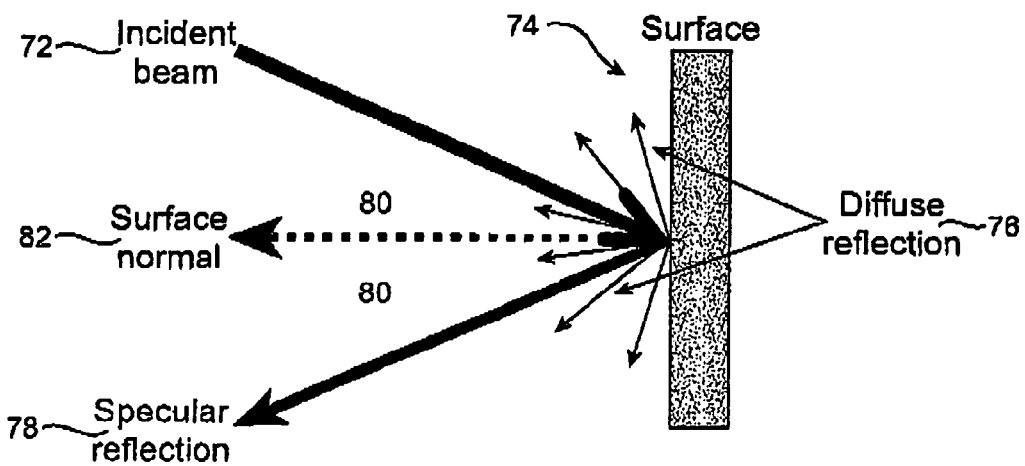
FIG. 4 schematically illustrates spectral and diffuse reflected light portions reflected by a surface.

The distance and/or angle measurements described herein will often make use of a specular light portion reflected from a target surface, as schematically illustrated in FIG. 4. When light (such as an incident light beam 72) strikes a surface (such as target surface 74), some of that light is absorbed, and some of the light is reflected. The light which is reflected off of surface 74 has two primary components: a diffuse reflected light portion 76, and a spectral reflected light portion 78. The diffuse reflected light portion spreads out over a wide angle, commonly being Lambertian. In contrast, the specular reflected light portion 78 leaves target surface 74 at the same angle as it struck the target surface. In other words, the specular reflected light portion 78 forms an angle 80 relative to the surface normal 82 which is the same as the angle formed by the incident light beam 72 relative to the surface normal. The percentages of light absorbed, light diffusely reflected, and light specularly reflected depend on the material properties of target surface 74 and on the wavelength of the incident light beam 72. Shiny or wet target surfaces generally have a higher spectral reflection component than do mat surfaces.

Figure 5:
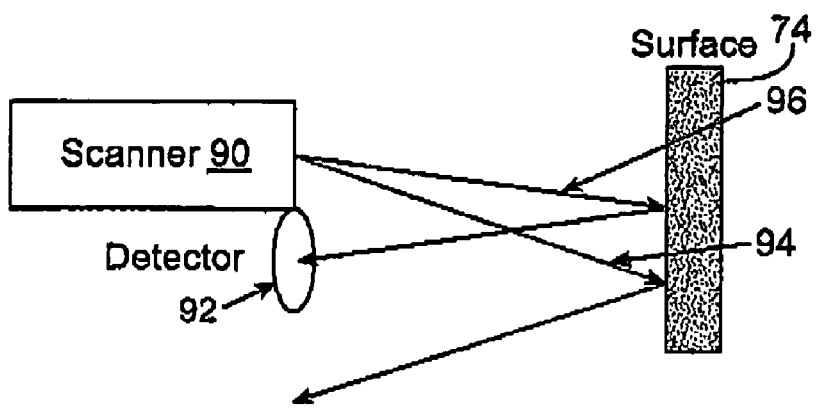
FIG. 5 is a simplified schematic illustrating a method for obtaining spatial relationship information from a spectral reflection using the system of FIG. 1.

Referring now to FIG. 5, a schematic distal end portion of scanned beam device 14 includes a scanner 90 (typically comprising a scanning element 34 as illustrated in FIG. 2) and a detector 92. Scanner 90 effects scanning of a light spot over a target surface 74. Detector 92 will often be used to generate an image of target surface 74 by detecting a diffuse portion of the reflected light as the light spot scans across the surface, thereby taking advantage of the wide distribution of the diffuse light. For measurement of distances and/or angles, in contrast, detector 92 may be used primarily for transmitting signals indicating the specular light portion incident on the surface of detector 92.

FIG. 5 illustrates a first scanned beam position 94 and a second scanned beam position 96, with these beam positions typically occurring at two different times during a scan. In the first scan position 94, the specular component of the reflected signal does not strike detector 92. Hence, in the first scan position 94, only diffuse reflected is received by detector 92, and the signals from the detector can be used to generate images of the target surface. In contrast, when the light beam from scanner 90 is at the second scan position 96 the specular component of the reflected light strikes detector 92. In this position, the detector receives both the diffuse light portion and the specular light portion of the reflected light. As the specular component that strikes the detector may have significantly higher energy than the diffused light component striking the detector, the detector's signal response may now be significantly greater. In some embodiments, the light at detector 92, when the light beam is in the second scan position 96, may be more than five times greater than when the light beam is at the first scan position 94; often being more than ten times greater, and in some cases being multiple orders of magnitude greater. Hence, separator 62 of controller 20 will often include a threshold for separation of the diffuse light portion from the spectral light portion. Unless the spectral light portion is separated from the overall signal at detector 92, a bright spot is created in the image of target surface 72. Threshold image processing techniques can be used to identify a perimeter of the spectral light portion, an area, a cross-sectional size, a centroid, and the like.

Figure 6A:
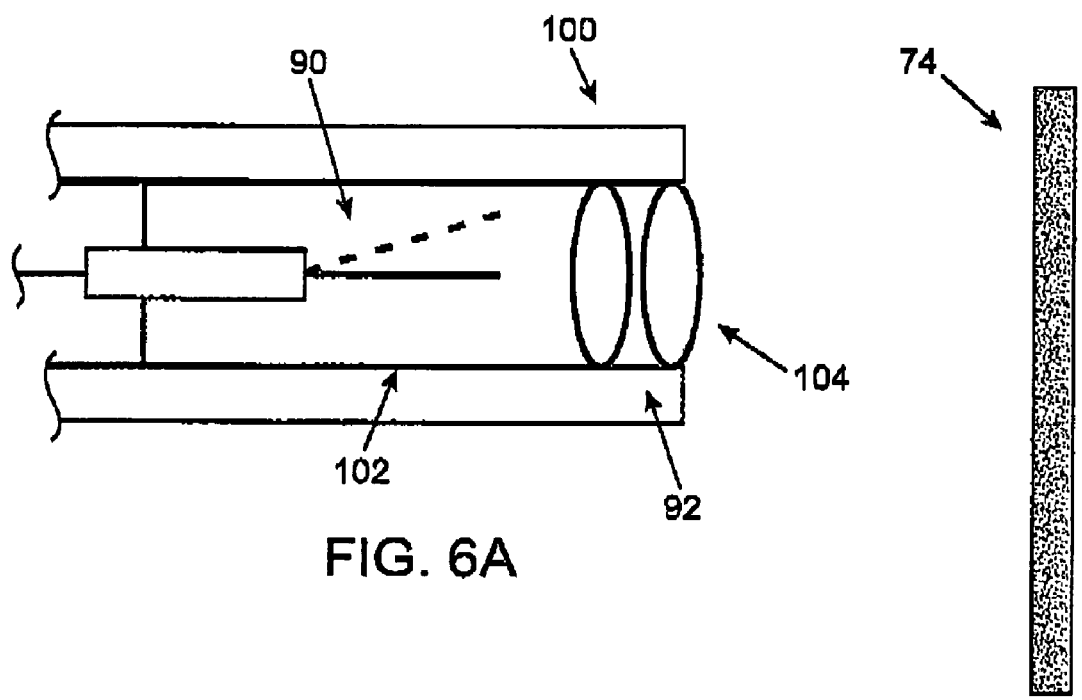
FIG. 6A is a schematic cross-sectional view of a distal portion of a probe for use in the system of FIG. 1.
Figure 6B:
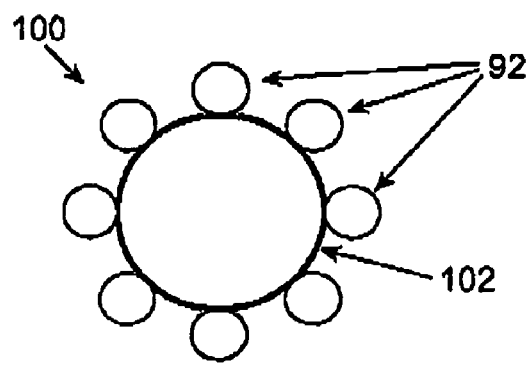
FIG. 6B is an end view of the probe of FIG. 6A, and illustrates an exemplary plurality of detectors for imaging and obtaining spatial measurement.

Referring now to FIGS. 6A and 6B, a probe 100 comprises a distal portion of a scanning beam device 14, as generally described above regarding FIGS. 1 and 2. Detector 92 here comprises eight optical fiber detectors with end surfaces distributed around an outer surface of the assembly of scanner 90. As can be seen in FIG. 6B, detectors 92 are shown disposed around an outer casing 102 of the scanner assembly, while one or more lenses 104 protect the scanner and/or improve optical properties of the scanned light. In other embodiments, at least some of detectors 92 may be disposed within casing 102.

When probe 100 of FIGS. 6A and 6B is used to image a surface that is normal to an axis of probe 100, an image similar to that shown in FIG. 7 may be generated. In the image of FIG. 7, eight bright spots 106 are formed by the specular reflection from target surface 74 striking each of the eight detectors 92. The eight bright spots 106 define a spectral reflection pattern 108, with the sensor pattern here being centered in the image. The location of the spectral pattern 108 at the center of the image of FIG. 7 results from the target surface 74 being normal to probe 100, and from the detectors 92 being symmetrically positioned about the scanning center of the scanner.

The specular reflection pattern can be problematic during the image formation using probe 100, as the high intensity of the spectral reflection relative to the diffuse reflected portion (on which the image is primarily based) tends to wash out or otherwise distort the desired image formation. Separation of the spectral light portion, identification of the spectral pattern, filtering, and/or other image processing steps may be taken to reduce the effects of spectral reflection in the displayed image of target surface 74.

The size of the spectral reflection pattern in FIG. 7 may be determined at least in part by the magnitude of the scan of scanner 90 during imaging (as expressed in angular field of view), and by the distance between the scanner and target surface 74. When scanning with a constant field of view, the spectral reflection pattern will be larger when the scanner is closer to the surface, as can be understood with reference to FIGS. 8A through 8C. Spectral reflection pattern 108a is similar to that of 108b and 108c, but is generally larger as the scanner 90 is closer to the target surface 74 (see FIG. 6A). Spectral reflection pattern 108b shrinks as the scanner moves away, and shrinks again (to the size of 108c) as the scanner 90 moves still farther away from target surface 74.

The relationship between the spectral reflection pattern size and the distance between probe 100 and target surface 74 can be used to determine the distance between the scanner (or other structure of the probe) and the surface. In this simple case, the target surface is assumed to be normal to the scan direction. In this case, only one sensor is required to determine a distance between probe 100 and surface 74.

An example of a probe/target surface distance calculation with a normal target surface can be understood with reference to FIG. 9. The following illustrated dimensions may 110 comprise system parameters which are known: Dsensor, the distance from the center of the scanner to the sensor of detector 92; θmax, the maximum field of view of the scanner; and Smax, the number of scan spirals that form an image (assuming a spiral scan pattern). Using these known parameters, the distance between the probe and the target surface Dsurface may be calculated by capturing the image and performing a binary threshold on the image data, so that pixels receiving specular reflections are assigned for example a binary value of 1, and those that do not receive specular reflections are assigned a binary value 0. With a single sensor, one connected image object (corresponding to the detector surface) should be identified. A pixel on which the center of this connected object lies (or is closest to) is determined, and remapping is used to determine the scan angle between the center of the image scan and the center or centroid of the connected object, Sc. In a relatively simple system having a linear angular scan, the scan angle θc is equal to (θmax*Sc)/Smax. In a more complex example, the scan angle can be saved in a remapping lookup table for each pixel.

The distance to the surface, Dsurface, is computed as:

$$D\text{surface} = D\text{sensor}/(2*\tan(\theta c)).$$

This relatively simple example assumes a spiral scan pattern for the sensor, with the size of the spiral gradually increasing and then decreasing rapidly. A variety of alternative scan patterns may be employed, with relatively straightforward adjustments to the distance calculation methodology. Where a plurality of detectors 92 are included in probe 100 and the target surface 74 remains normal to the probe, the distance between the probe and target surface can be determined for each sensor using the methodology described above, with the results averaged to reduce error.

Figure 10:
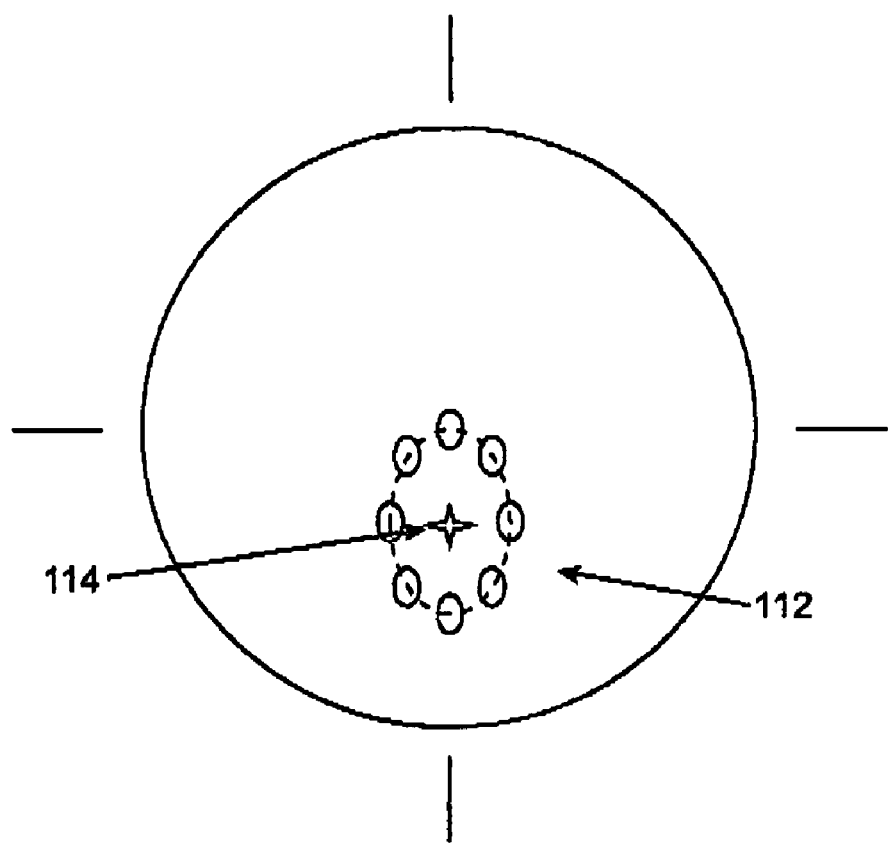
FIG. 10 schematically illustrates a change in shape and location of both a spectral reflection pattern and each individual spectral reflection within the pattern with a change in angle between the probe and the target surface.
Figure 11:
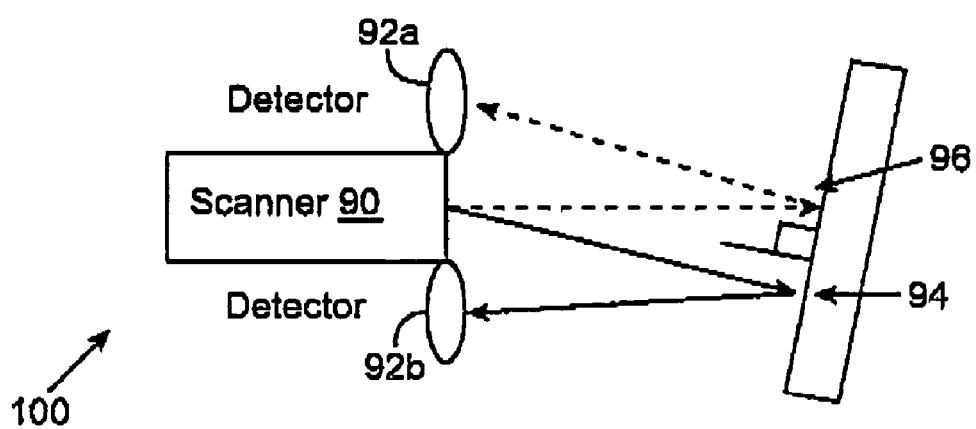
FIG. 11 illustrates a shift in location of the spectral reflection with changes in an angle of the target surface relative to the probe.

Referring now to FIGS. 10 and 11, a slightly more complex case assumes that the target surface 74 is flat but tilted in an angle relative to the probe 100. Assuming the circular arrangement of sensors of FIGS. 6A and 6B are used, a spectral light pattern 112 may have a non-symmetric shape, and may also have a centroid 114 which is offset from a center of the image, as illustrated in FIG. 10. As the detectors 92A, 92B remain symmetrically distributed about scanner 90, the flat target surface may generate similar spectral light reflection angles, so that the centroid 114 of pattern 112 may map to an angle between probe 100 and the target surface. Hence, calculations similar to those above may be used to determine the relative angle between the target surface and the probe. Alternative embodiments may employ a lookup table based on the pixel location of centroid 114 to identify the relative angle of the target surface.

Still more complex analysis may be possible. For example, spectral reflection pattern 112 may be analyzed using the centroids of each of the discreet continuous image objects, as schematically illustrated by the ellipse in FIG. 10. As described above, this may allow identification of a tilt angle of an assumed-flat target surface. Additionally, each individual image object generated by an associated detector may be treated as a spectral pattern, and analysis of these individual sub-patterns (including analysis of their centroid positions, shapes, and sizes) may allow a local distance between the probe 100 and the target surface to be identified, a local angle of the target surface relative to the probe to be determined, and/or the like, for example, by at least initially, assuming that the target surface within each spectral object is flat. Hence, curved target surfaces may be geometrically measured using the spectral pattern distortion, scaling, and size. Although somewhat more complex, by appropriate positioning of the sensors and with proper analysis (and/or careful empirical studies of a wide variety of surface distances and angles), a variety of distance and angle information can be gathered.

A variety of features and refinements may be included in system 10 to enhance the accuracy and capability of the spatial relationship measurement. For example, the maximum angular scan magnitude of the scanning beam device may be smaller during geometrical or spatial relationship measurements than during at least some imaging operations. This may allow greater precision in determining the scan angle for a specular reflection of any given detector. In some embodiments, detectors may be placed at different distances from the center of the scan, for example, with another circumferential row of detectors disposed around the detectors illustrated in FIGS. 6A and 6B. This slightly more complex pattern of detectors may assist in gathering surface shape information, with any subset of the detectors optionally being used together to identify local angles and distances of the target surface. The sizes of the specular reflection spots in an image may be analyzed, with (for example) shorter probe/target surface separation distances generally generating larger reflected spectral spot sizes. As mentioned above, the shape of the individual spectral spots or objects in the image may be also be analyzed, with distortion in a spot pattern shape indicating a surface tilt, such as a round detector surface producing an elliptical or teardrop shaped spectral reflection. Analyzing the individual spots in a pattern with multiple spectral reflection spots can help determine the tilt at multiple points over a surface. From this information, overall surface shape can be derived and distance more accurately determined.

Still more complex, accurate, and/or complete methods and systems may also be employed. For example, the tip of the probe 100 may be moved to gather spectral information from a plurality of images at a plurality of locations. The movement may be effected as part of the natural movement of an endoscope tip down a lumen over time, or a deliberate motion of the tip may be employed to gather surface shape information. The information from different images can be combined to create a more accurate contour map of the surface. In some embodiments, position tracking of the tip of probe 100 may be employed, such as by including magnetic or other known and/or commercially available position signal generators in or adjacent the probe tip. Such structures may allow a fixed frame of reference to be identified and combined with distance and/or angular measurements based on specular reflections obtained with different probe tip locations. Non-specular surface images can be used to help determine a distance the tip has moved, such as by identifying one or more datum features or locations in an image and tracking the differences in the location of that datum feature or image relative to the probe before and after movement. Detectors or sensors of different shapes may also be employed, for example, with a detector surface which is square rather than circular. This may increase the information obtained from analysis of the specular spot shape.

Figure 12:
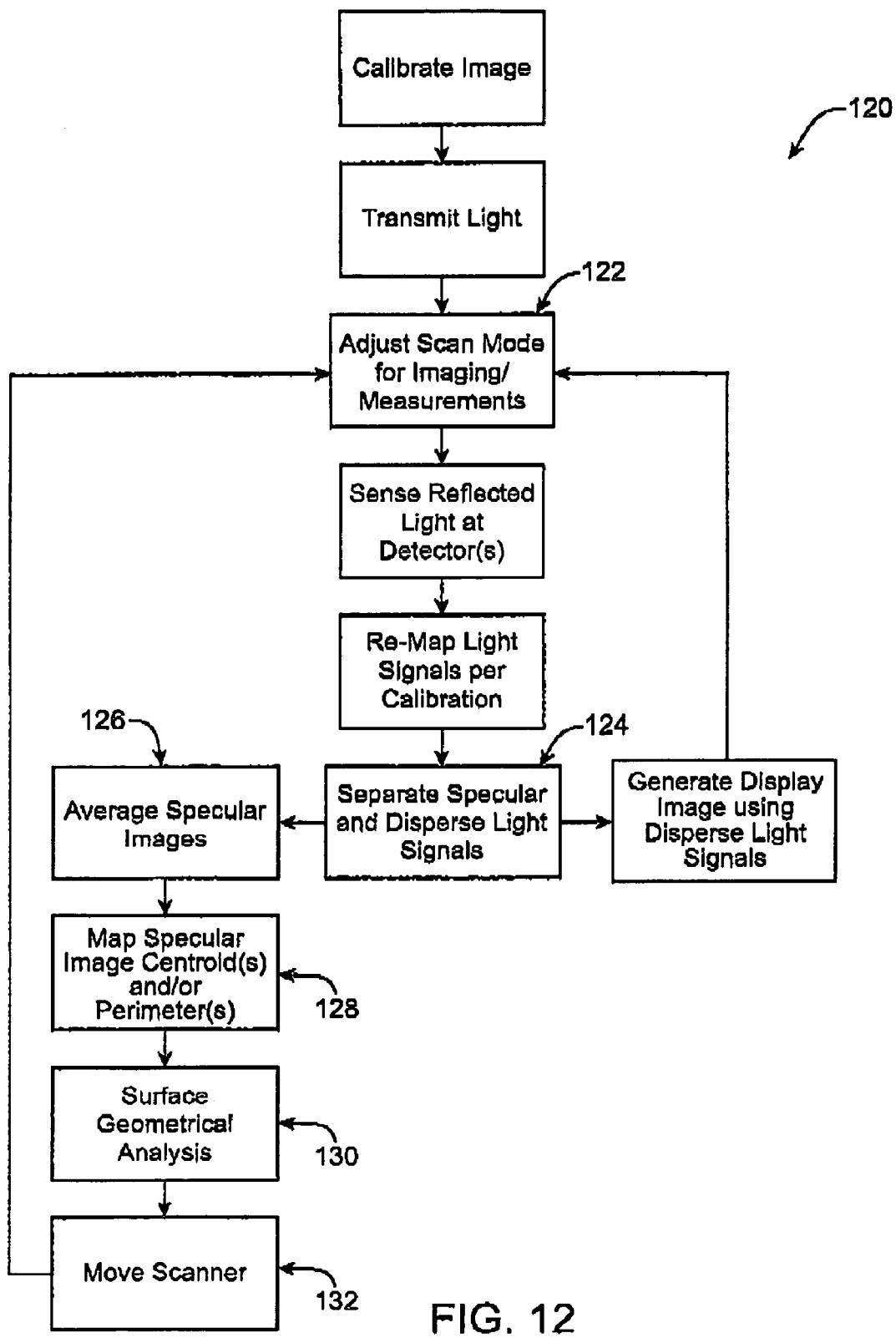
FIG. 12 is a flowchart schematically illustrating a method for identifying spatial relationships between a scanned beam probe and a target surface.

Referring now to FIG. 12, a method 120 for using system 10 of FIG. 1 to both image and obtain distance and/or angle measurements is shown. Image calibration, light transmission from the end of the fiber, sensing of reflected light, and remapping of the light signals for generation of an image may be performed according to the previously described scanning beam device techniques, per the references cited above (as previously incorporated herein by reference).

To obtain measurements in method 120, the scan mode may optionally be adjusted 122, often to limit the scan angle and field of view to be smaller than those of some or all image capture scans. The measurement scan will preferably still encompass some or all of the specular reflected light pattern, with the smaller scan angle increasing measurement resolution.

The sensed and remapped reflected light signals will often be separated into a disperse light portion and a specular light portion 124, typically using an intensity threshold. The threshold may be pre-set, or may be determined from the characteristics of the light signals prior to separation. Specular light portion images from a plurality of scans will be averaged 126, and characteristics of specular image objects (such as the shape of one or more perimeter, the location of one or more centroid, shapes defined by a plurality of centroids, and the like) may be identified and mapped 128 using any of a wide variety of image processing and analysis software packages. These characteristics may then be used for a spatial or geometrical analysis 130 of the surface(s) within the field of view of the probe that generate the spectral reflections. As described above, the analysis will often be based at least in part on the geometry of the probe(s) that transmit and/or receive the reflected spectral light, and/or on the symmetry between the angle of incident light and the angle of spectral reflection about the surface normal. Optionally, after movement of the scanner and/or detector, and often the entire probe 132, another measurement and/or imaging cycle may be initiated.

All the exemplary embodiments have been described in some detail by way of example and for clarity of understanding, a variety of modifications, changes, and adaptations will be obvious to those of skill in the art. Hence, the scope of the present invention is limited solely by the appended claims.

What is claimed is:

1. A method for determining a spatial relationship between a probe and a target surface, the method comprising:

scanning a beam of light from the probe spatially across the surface;

sensing, with a light detector of the probe, a specular reflection of the light from the surface, the sensed specular reflection comprising specular image signals;

determining a specular reflection pattern from the specular image signals; and determining a distance between the surface and the probe or an angle between the surface and the probe using at least a geometric characteristic of the specular reflection pattern.

2. The method of claim 1, wherein the probe comprises an endoscope, and wherein the surface comprises a tissue surface within a patient body.

3. The method of claim 1, wherein the beam is oscillated by vibrating an optical fiber with a two-dimensional scan.

4. The method of claim 1, wherein the beam of light comprises an imaging light beam, the probe transmitting imaging signals for imaging the surface in response to diffuse reflection of the light beam from the surface.

5. The method of claim 4, further comprising detecting the specular light and the diffuse light with the detector, and separating specular image signals from display image signals using a brightness threshold, the sensed specular reflection comprising the specular image signals.

6. The method of claim 4, wherein an angular scan magnitude is smaller when measuring the specular reflection than when imaging.

7. The method of claim 1, wherein the distance or angle is determined from an angle of the scanning beam when the specular reflection is sensed.

8. The method of claim 7, further comprising scanning the beam with a scanner, wherein the distance is determined using a scanner/detector distance between the scanner and the detector.

9. The method of claim 8, wherein the scanner/detector distance comprises a distance between a center of the scanner and the detector.

10. The method of claim 8, further comprising sensing the specular reflection with a plurality of light detectors of the probe, and determining a pattern of spectral reflections from the surface as sensed by the plurality of detectors.

11. The method of claim 10, wherein the distance is further determined in response to a spectral reflection pattern size.

12. The method of claim 8, wherein the detector is at a first distance from a center of the scan, and wherein another detector is at a second distance from the center of the scan, the second distance being different than the first distance.

13. The method of claim 1, further comprising determining the angle of the surface relative to the probe using the specular reflection.

14. The method of claim 13, wherein the angle is determined at least in part from a shape of the spectral reflection.

15. The method of claim 14, wherein the shape of the spectral reflection comprises:
a spectral reflection pattern shape within an image received by a pattern of detectors, or
a single spectral reflection outline shape received at a single detector.

16. The method of claim 14, wherein the angle of the surface relative to the probe is measured at a plurality of locations within a field of view of the probe.

17. The method of claim 1, further comprising moving a scanner of the probe from a first location to a second location, the scanning beam of light being transmitted from the scanner, the specular light reflections being measured with the scanner at the first and second locations.

18. The method of claim 17, wherein the scanner is moved between a first measurement at the first location and a second measurement at the second location by moving the probe.

19. The method of claim 18, wherein the processor identifies a datum location for the first measurement, identifies the datum location for the second measurement, and uses the datum location to combine the first and second measurements.

20. The method of claim 17, further comprising imaging the surface with the scanner at the first and second locations and generating a contour map of the surface using at least one of the images or the measured specular reflections.

21. The method of claim 1, wherein the light detector has a non-round light detection surface.

22. The method of claim 1, further comprising generating a plurality of images of the surface from signals transmitted by the detector and averaging the images to enhance accuracy of the distance or angle determination.

23. The method of claim 1, wherein the distance between the surface and the probe is determined using a size of a single spectral reflection received at a single associated detector.

24. A surface measurement system comprising:
a light source for transmitting a beam of light;
a scanner coupled to the light source, the scanner spatially scanning the beam of light over a surface;
a light detector positioned to detect a specular reflected portion of the light from the surface, the detected specular reflection portion comprising specular image signals; and
a processor coupled to the detector, the processor configured to determine:
a specular reflection pattern from the specular image signals; and
a distance between the surface measurement system and the surface, or an angle of the surface relative to the surface measurement system, from at least a geometric characteristic of the specular reflection pattern.

25. The surface measurement system of claim 24, wherein at least the scanner and the light detector are included within an endoscopic probe body.

26. The surface measurement system of claim 24, wherein the scanner comprises an assembly including a fiber and an actuator system for oscillating the fiber in first and second dimensions, the assembly suitable for use in a scanning fiber endoscope system.

27. The surface measurement system of claim 24, wherein the processor comprises a separator module configured to separate the specular reflected light from diffuse reflected light.

28. The surface measurement system of claim 27, further comprising a display coupled to the processor, the display showing an image of the surface generated using the diffuse reflected light.

29. Software for use in a scanned beam imaging system, the system including a scanner configured for spatially scanning a beam of light over a target surface, a detector positioned for detecting reflected light from the surface, the light comprising a specular reflected portion, and the detected specular reflected portion comprising specular image signals, and a processor coupled to the detector, the software comprising a tangible computer readable media comprising machine readable code embodying instructions that, if executed, cause the processor to determine:
a specular reflection pattern from the specular image signals; and
a distance between the system and the surface, or an angle of the surface relative to system, using at least a geometric characteristic of the specular reflection pattern.

* * * * *